United States Patent [19]

Lea Plaza

[11] Patent Number: 4,875,471

[45] Date of Patent: * Oct. 24, 1989

[54] DEVICE FOR CORRECTING DEFORMITIES OF THE SPINE

[75] Inventor: Carlos Lea Plaza, Montevideo, Uruguay

[73] Assignee: Codespi Corporation, Fla.

[*] Notice: The portion of the term of this patent subsequent to Apr. 19, 2005 has been disclaimed.

[21] Appl. No.: 167,914

[22] Filed: Mar. 14, 1988

Related U.S. Application Data

[63] Continuation-in-part of Ser. No. 17,050, Feb. 20, 1987, Pat. No. 4,738,251.

[51] Int. Cl.$^4$ ............................................. A61B 17/56
[52] U.S. Cl. .......................................... 128/69; 128/68
[58] Field of Search ................................ 128/69, 92, 68

[56] References Cited

U.S. PATENT DOCUMENTS

| 4,505,268 | 3/1985 | Sgandurra | 128/69 |
| 4,686,970 | 8/1987 | Dove et al. | 128/69 |
| 4,738,251 | 4/1988 | Plaza | 128/69 |

FOREIGN PATENT DOCUMENTS

| 870253 | 12/1974 | U.S.S.R. | 128/69 |
| 0624615 | 9/1978 | U.S.S.R. | 128/69 |
| 0850062 | 7/1981 | U.S.S.R. | 128/69 |
| 1063404 | 12/1983 | U.S.S.R. | 128/69 |

Primary Examiner—Paul T. Sewell
Assistant Examiner—Huong Q. Pham
Attorney, Agent, or Firm—Jesus Sanchelima

[57] ABSTRACT

A device for stabilizing and correcting deformations of the spine being surgically mountable over the vertebrae and having substantially the shape of a rectangular frame that extends over the length of the vertebrae to be corrected. The device includes two elongated rigid members kept in a spaced apart relationship by rigid curved members on the approximate ends and spacer members in between. The curved members are mounted at a position that is slightly separated from the ends of the elongated members and in cooperation with hook members that are positioned on the outer periphery of the elongated members receive tying wires that secure the vertebrae to the frame maintaining the former in the corrective configuration.

4 Claims, 1 Drawing Sheet

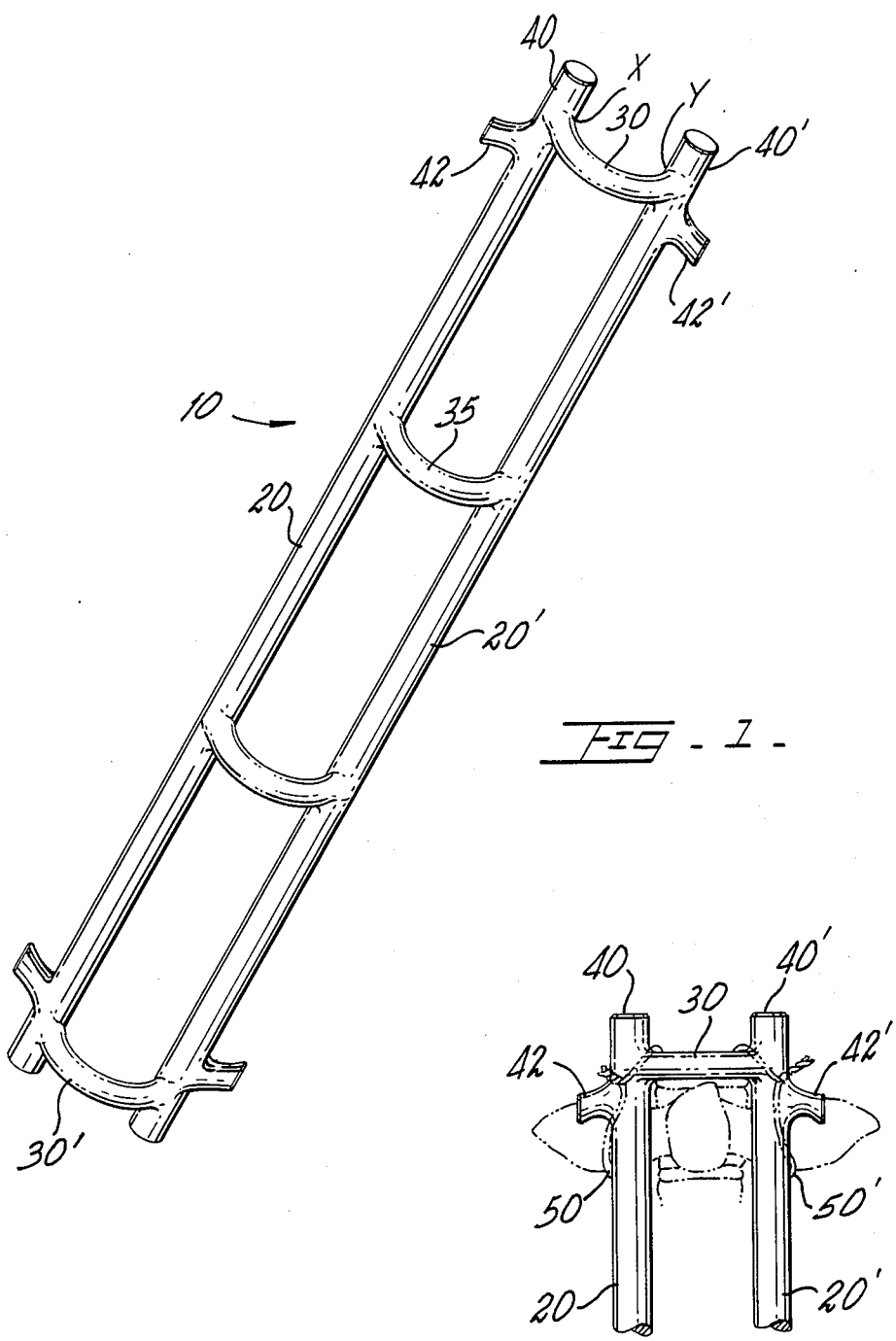

DEVICE FOR CORRECTING DEFORMITIES OF THE SPINE

BACKGROUND OF THE INVENTION

1. Field of the Invention

The present invention relates to a device for surgically correcting and stabilizing spine deformations, and more particularly, to such a device that effectively provides support to the vertebrae affected.

2. Other Related Applications

The present application is a continuation-in-part of allowed and pending U.S. patent application Ser. No. 017,050, U.S. Pat. No. 4,738,251 filed on Feb. 20, 1987, which is hereby incorporated by reference.

3. Description of the Related Art

The device claimed in the above-referenced parent application has been modified to further improve the efficiency of the device by adding structural integrity and improving its anchoring on the spine.

Other patents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a spinal framing device for surgical correction of spinal deformities, that can surgically correct and stabilize severe deformations of the spine, stabilize fractures of vertebrae and reduce dislocations.

It is another object of the present invention to provide a device that can be used on any section of vertebrae of the spine, particularly such sections that include more than five vertebrae.

It is still another object of this invention to provide a device that is capable of rotating the vertebrae back to the normal position, or approach it, while the deformity is being corrected simultaneously with the same device.

It is yet another object of this invention to provide such a device that includes more effective and reliable attachment to the spine.

It is yet another object of the present invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1 represents an elevational view in perspective of the spinal framing device.

FIG. 2 shows a detailed view of one of the devices shown in FIG. 1.

DETAILED DESCRIPTION OF THE PREFERRED EMBODIMENT

Referring now to FIG. 1, it can be observed that the present invention is generally referred to with numeral 10. As in the parent application, device 10 includes two elongated rigid members 20 and 20', parallel to each other and spaced apart by two curved rigid members 30 and 30' that are rigidly mounted on the ends of members 20 and 20'. Members 20 and 20' include each two ends where curved rigid members 30 and 30' are rigidly mounted, preferably soldered. The curvature of members 30 and 30' is such that they substantially accommodate to the anatomy of the posterior spine. Obviously, the radius of curvature of members 30 and 30' will be different for cervical vertebrae than for thoracic or lumbar vertebrae.

It is important to note that when the wires are tightened, distraction is produced at the ends of the spine section and a lateral traction force is applied at the middle of the deformed section, thereby obtaining correction of the deformity. Also, de-rotation of the vertebrae is intended and the spine is brought back to the middle line which should be parallel to elongated members 20 and 20'. The term 'middle line' means the axis of the spine that defined by a line connecting the occipitaal and sacral bones. The length of members 20 and 20' will vary, but if it exceeds the span of five vertebrae, approximately, it will require a spacing member 35 to ensure the effective derotation of the deformed section. If one spacing member 35 is not used for spans of five vertebrae or fraction thereof, the parallel orientation of members 20 and 20' may be affected with time and constant forces being applied by the deformed spine overcoming the structural integrity of device 10.

Another improvement of the present invention over the above-referenced parent application involves the use of the ends 40 and 40' that cooperate with hook members 42 and 42' to provide the necessary anchorage point for wires 50 and 50'. A characteristic of this new design is smoother contours around hook member 40 which, in the parent application, had to be filed before and not infrequently leaving sharp areas that tended to cut through wires 50 and 50' at points X and Y, especially after several years of use and fatigue of wires 50 and 50'. This feature has improved the reliability of the device markedly and also facilitated its production in quantities. The shape of ends 30 and 40' do not have a wedge shape and hook members 42 and 42' do not have an accentuated wedge shape. Rather, the shape of these members are devoid of sharp edges, thereby avoiding secondary operations in the production line.

It is believed the foregoing description conveys the best understanding of the objects and advantages of the present invention. Different embodiments may be made of the inventive concept of this invention. It is to be understood that all matter disclosed herein is to be interpreted merely as illustrative, and not in a limiting sense.

What is claimed is:

1. A device for stabilizing and correcting deformations of the spine being surgically mountable over the vertebrae and said correction includes bringing the spine back to its center line de-rotated, comprising:
   A. two elongated rigid members parallel to each other and each member having two ends;
   B. two curved rigid members rigidly mounted to said elongated members so that said elongated members are kept in a spaced apart relationship from each other and said elongated and curved members form a rigid rectangular frame and said curved rigid members mounted at a point slightly separated from said ends;
   C. two hook members mounted on the outer periphery of said elongated members substantially towards the ends of said elongated members and adjacent to where said curved member is mounted on said elongated member;

D. a curved spacer member having a curved shape and rigidly mounted between said elongated members thereby reinforcing the structural integrity of said frame, said curved rigid members and said curved spacer member being smoothly curved for the entirety of their extent between said elongated members;

E. wire means for tying said device to the vertebrae by using said hook members and said ends of said elongated members as anchorage points.

2. The device set forth in claim 1 wherein said curved rigid and spacer members are made out of stainless steel.

3. The device set forth in claim 2 wherein the radius of curvature of said curved rigid and spacer members follow the contours of said vertebrae.

4. The device set forth in claim 3 wherein said hook members and said ends provide a smooth anchorage area for said wire means, thereby accomplishing derotation of the vertebrae when urging the spine towards the middle line of the spine and providing better rotatory stability to the spine.

* * * * *